United States Patent
Bright et al.

(10) Patent No.: US 11,236,324 B2
(45) Date of Patent: Feb. 1, 2022

(54) ISOLATION OF STEM CELLS FROM ADIPOSE TISSUE BY ULTRASONIC CAVITATION, AND METHODS OF USE

(71) Applicant: Cell-Innovations IP Pty Ltd, Newcastle (AU)

(72) Inventors: Ralph Bright, Liverpool (AU); Pelin Bright, Liverpool (AU); Bruce Hansen, Liverpool (AU); Wayne Thomas, Liverpool (AU)

(73) Assignee: Cell-Innovations IP Pty Ltd, Newcastle (AU)

( * ) Notice: Subject to any disclaimer, the term of this patent is extended or adjusted under 35 U.S.C. 154(b) by 203 days.

(21) Appl. No.: 16/019,171

(22) Filed: Jun. 26, 2018

(65) Prior Publication Data
US 2019/0002867 A1 Jan. 3, 2019

Related U.S. Application Data

(63) Continuation of application No. 14/409,229, filed as application No. PCT/AU2013/000686 on Jun. 26, 2013, now abandoned.

(30) Foreign Application Priority Data

Jun. 26, 2012 (AU) ................. 2012902719

(51) Int. Cl.
| | | |
|---|---|---|
| C12N 13/00 | (2006.01) | |
| C12N 1/06 | (2006.01) | |
| C12N 5/0775 | (2010.01) | |
| A61K 35/35 | (2015.01) | |

(52) U.S. Cl.
CPC .............. *C12N 13/00* (2013.01); *A61K 35/35* (2013.01); *C12N 1/066* (2013.01); *C12N 5/0667* (2013.01); *C12N 2521/10* (2013.01)

(58) Field of Classification Search
None
See application file for complete search history.

(56) References Cited

U.S. PATENT DOCUMENTS

| | | |
|---|---|---|
| 2006/0051865 A1 | 3/2006 | Higgins et al. |
| 2012/0164113 A1 | 6/2012 | Victor |

FOREIGN PATENT DOCUMENTS

| | | |
|---|---|---|
| CN | 201752668 U | 3/2011 |
| WO | WO-2005/035742 A2 | 4/2005 |
| WO | WO-2011/069060 A2 | 6/2011 |

OTHER PUBLICATIONS

Bucco, "Adipose-derived stem cells for regenerative medicine: yield of stromal vascular fraction from liposuction or lumbar resection," Scientifica Acta, 3(2):73-5 (2009).
Chinese Office Action in Patent Application No. 201380044693.8 dated Apr. 14, 2016.
Chinese Office Action in Patent Application No. 201380044693.8 dated Dec. 30, 2016.
Chinese Office Action in Patent Application No. 201380044693.8 dated Jul. 21, 2017.
European Search Report and Opinion from European application No. EP 13810843 dated Jan. 18, 2016.
Gibbs et al., "Management of knee osteoarthritis by combined stromal vascular fraction cell therapy, platelet-rich plasma, and musculoskeletal exercises: a case series," J Pain Res, 2015(8):799/806 (2015).
Hielscher UP200S Product Information, pp. 1-4, retrieved from the Internet, Feb. 22, 2017: www.hielscher.com/200s_p.htm.
Hielscher UP200S/UP400S Instruction Manual, pp. 1-36, retrieved from the Internet Feb. 23, 2017: www.bendarygroup.com/images/instruction_manual_up200_400s_2007_ultrasonics.pdf.
International Search Report for PCT/AU2013/000686 dated Aug. 23, 2013.
Japanese Office Action in Patent Application No. 2015-518723 dated Apr. 26, 2017.
Nakagami et al., "Adipose tissue-derived stromal cells as a novel option for regenerative cell therapy," J Atheroscler Thromb, 13(2):77-81 (2006).
Office Action from the New Zealand Intellectual Property Office dated Mar. 31, 2017 (IP No. 703318).
Office Action from the New Zealand Intellectual Property Office dated Sep. 15, 2016 (IP No. 703318).

*Primary Examiner* — Scott Long
*Assistant Examiner* — Evelyn Y Pyla
(74) *Attorney, Agent, or Firm* — Foley Hoag LLP

(57) ABSTRACT

In one embodiment, the present invention relates to a non-enzymatic method for isolating stem cells from adipose tissue, wherein the method comprises treating adipose tissue with ultrasonic cavitation to break up the adipose tissue and lyses mature adipocytes, resulting in a stromal vascular fraction containing viable stromal/stem cells.

9 Claims, 4 Drawing Sheets

ISOLATION OF STEM CELLS FROM ADIPOSE TISSUE BY ULTRASONIC CAVITATION, AND METHODS OF USE

CROSS REFERENCE TO RELATED APPLICATIONS

This application is a continuation of U.S. application Ser. No. 14/409,229, filed on Dec. 18, 2014, which is a 371 national stage application of PCT/AU2013/000686, filed on Jun. 26, 2013, which claims priority from Australian Provisional Application No. 2012902719, filed on Jun. 26, 2012, the contents of which are incorporated herein by reference in their entirety.

FIELD OF THE INVENTION

The present invention relates to methods of utilizing stem cell preparations.

The invention has been developed primarily for the non-enzymatic isolation of stromal/stem cells from adipose tissue and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Adipose tissue, in addition to containing mature adipocytes, also contains stem cells that can be differentiated into a variety of cell lineages (Zuk et al. Tissue Eng. 2001; 7: 211-228; Hicok et al. Tissue Eng. 2004; 10: 371-380; Erickson et al. Biochem Biophys Res Commun. 2002; 290: 763-769; Cousin et al. Biochem Biophys Res Commun. 2003; 301: 1016-1022; Safford et al. Biochem Biophys Res Commun. 2002; 294: 371-379; Miranville et al. Circulation. 2004; 1 10: 349-355; Planat-Benard et al. Circ Res. 2004; 94: 223-229; Planat-Benard et al. Circulation. 2004; 1 09: 656-663). The stem cells are adhesive and can proliferate in culture. Accordingly, a large number of stem cells can be obtained from a small amount of adipose tissue.

Presently in order to isolate stem cells from adipose tissue, enzymes such as collagenase are typically used to dissolves the bonds in the collagen that hold together the adipose tissue (see, e.g., Zuk, et al. Mol Biol Cell. 2002; 13: 4279-4295; Zuk, et al. Tissue Eng. 2001; 7: 211-228). While collagenase is effective, it can be unsuitable for preparing stem cells as:

enzyme treatment results in a high level of cell death, thereby reducing numbers of isolated stem cells and resulting in more cellular debris;
enzymes may damage and destroy unique cell types;
contamination of isolated stem cells with enzymes may make them unsuitable for transplantation; and
regulatory bodies may consider that the use of enzymes in the isolation of stem cells results in a cellular product requiring drug approval.

It is an object of the present invention to overcome or ameliorate at least one of the disadvantages of the prior art, or to provide a useful alternative.

SUMMARY OF THE INVENTION

Surprisingly, the present inventors have found that treating adipose tissue with ultrasonic cavitation breaks up the adipose tissue and lyses mature adipocytes, resulting in a stromal vascular fraction comprising viable stem/stromal cells and extra cellular matrix.

In one aspect, the present invention relates to isolating a stromal vascular fraction comprising viable stromal/stem cells and extracellular matrix from adipose tissue, the method comprising treating the adipose tissue with ultrasonic cavitation for a time, amplitude and cycle sufficient to break up the tissue and lyse mature adipocytes while maintaining the viability of the stromal/stem cells.

The ultrasonic cavitation amplitude and cycle settings may be variable and are dependent on the quantity of adipose tissue and timing of the process to maintain cell viability. The cell viability temperature range should not be exceeded.

In another aspect, the temperature of the adipose tissue during ultrasonic cavitation is maintained at a temperature that ensures the viability of the stromal/stem cells.

In another aspect, the temperature of the adipose tissue does not exceed about 43° C. to about 45° C.

In another aspect, the adipose tissue is treated with ultrasonic cavitation for a period of about 10 seconds to about 10 min with an ultrasonic device set at amplitude about 20 to about 75% and cycle about 0.2 to about 0.9.

In another aspect, an ultrasonic cavitation device probe is placed the adipose tissue, amplitude is set at about 50%, the cycle is set at about 0.4 to about 0.5 and the probe is raised and lowered through the adipose tissue for about 1 minute and 30 seconds to about 1 minute and 40 seconds; and wherein the temperature of the adipose tissue is maintained at a temperature lower than about 43° C. to about 45° C.

In another aspect, the present invention relates to a stromal vascular fraction comprising viable stem cells isolated according to the method of the invention.

In another aspect, the stromal vascular fraction comprises viable cells other than stem cells.

In another aspect, the present invention relates to adipose tissue-derived stem cells isolated according to the method of the invention.

In another aspect, the present invention relates to a method of treating osteoarthritis, a joint-related inflammatory disorder, an inflammatory arthritis disorder, soft-tissue damage or tears, a cartilage disorder, a bone disorder, an auto-immune disorder, muscle dystrophy, chronic fatigue, a lung disorder, a lung inflammatory disorder, a nervous system disorder, a spinal disorder or a neurological disorder in a subject comprising administering to the subject adipose tissue-derived stromal/stem cell preparations according to the invention.

In another aspect, the present invention relates to use of adipose tissue-derived stromal/stem cell preparations according to the invention for the manufacture of a medicament for treating osteoarthritis, a joint-related inflammatory disorder, an inflammatory arthritis disorder, soft-tissue damage or tears, a cartilage disorder, a bone disorder, an auto-immune disorder, muscle dystrophy, chronic fatigue, a lung disorder, a long inflammatory disorder, a nervous system disorder, a spinal disorder or a neurological disorder.

In another aspect, the present invention relates to adipose tissue-derived stromal/stem cell preparations according to the invention for use in the treatment of osteoarthritis, a joint-related inflammatory disorder, an inflammatory arthritis disorder, soft-tissue damage or tears, a cartilage disorder, a bone disorder, an auto-immune disorder, muscle dystrophy, chronic fatigue, a lung disorder, a lung inflammatory disorder, a nervous system disorder, a spinal disorder or a neurological disorder.

In another aspect, the present invention relates to a method of isolating a stromal vascular fraction comprising viable stromal/stem cells from adipose tissue comprising treating the adipose tissue with ultrasonic cavitation for about 1 minute and 30 seconds to about 1 minute and 40 seconds with an ultrasonic device set at an amplitude and cycle that ensures that the temperature of the adipose tissue does not exceed about 43° C. to about 45° C.

In another aspect, the present invention relates to a method of isolating a stromal vascular fraction comprising viable stromal/stem cells from adipose tissue comprising treating the adipose tissue with an ultrasonic device set at an amplitude of about 50%, wherein the device is set at a cycle and applied for a time that ensures that the temperature of the adipose tissue does not exceed about 43° C. to about 45° C.

In another aspect, the present invention relates to a method of isolating a stromal vascular fraction comprising viable stromal/stem cells from adipose tissue comprising treating the adipose tissue with an ultrasonic device set at a cycle about 0.4 to 0.5, wherein the device is set at an amplitude and applied for a time that ensures that the temperature of the adipose tissue does not exceed about 43° C. to about 45° C.

In another aspect, the present invention relates to a method of isolating a stromal vascular fraction comprising viable stromal/stem cells from adipose tissue comprising treating the adipose tissue with ultrasonic cavitation for about 1 minute and 30 seconds to about 1 minute and 40 seconds with an ultrasonic probe set at amplitude about 50% and cycle about 0.4 to about 0.5.

In another aspect, the present invention relates to a method for maintaining viability of stromal/stem cells in the stromal vascular fraction isolated from adipose tissue by ultrasonic cavitation, wherein time, amplitude and cycle of ultrasonic cavitation are selected such that the stromal/stem cells are viable after 48 hours cell culture.

As used herein, the term "adipose tissue" refers to any fat tissue. The adipose tissue may be brown or white adipose tissue. Preferably, the adipose tissue is subcutaneous white adipose tissue. The adipose tissue may be from any organism having fat tissue. Preferably the adipose tissue is mammalian, most preferably the adipose tissue is human. A convenient source of human adipose tissue is that derived from liposuction surgery or other surgery. However, the source of adipose tissue or the method of isolation of adipose tissue is not critical to the invention.

As used herein the term "stromal vascular fraction" refers to a fraction, comprising cells, derived from blood vessels and surrounding tissue found in adipose tissue. The fraction may comprise different cell types including, by way of example, mesenchymal stem cells, early mesenchymal/stromal precursor cells, adipose tissue-derived stem cells, Muse-AT cells, hematopoietic cells, hematopoietic stem cells, platelets, Kupffer cells, osteoclasts, megakaryocytes, granulocytes, NK cells, endothelial precursor or progenitor cells, pluripotent cells, CD34+ cells, Stro-1+ cells, Stro-3+ cells, CD166+ cells, Thy-1+ or CD90+ stem cells, CD44+ cells, immune cells such as monocytes, leukocytes, lymphocytes, B and T cells, NK cells, macrophages, neutrophil leukocytes, neutrophils, neutrophil granulocytes, and the like. The stromal vascular fraction also includes cells expressing any of the markers or any combination thereof disclosed herein. As used herein, the term "stromal vascular fraction" includes within its scope terms such as "mesenchymal vascular fraction", "mesenchymal fraction", "stromal fraction" and the like.

As used herein, the term "mesenchymal stem cell" refers to stromal or mesenchymal cells or early mesenchymal/stromal precursor or dispose tissue-derived stromal/stem cells which are multipotent and can serve as stem cell-like precursors to a variety of different cell types such as but not limited to adipocytes, osteocytes, chondrocyte, muscle and neuronal/glial cell lineages.

Mesenchymal stem cells make up a subset population derivable from, for example, adipose tissue and bone marrow. As used herein, the term "mesenchymal stem cell" includes within its scope terms such as "stromal stem cell", "marrow stromal cell", "multipotent stromal cell", "mesenchymal precursor cell", "Muse-AT", adipose tissue-derived stromal/stem cells and the like.

As used herein, the term "differentiated" refers to a cell that has achieved a terminal state of maturation such that the cell has developed fully and demonstrates biological specialization and/or adaptation to a specific environment and/or function. Typically, a differentiated cell is characterized by expression of genes that encode differentiation-associated proteins in that cell. For example expression of GALC in a leukocyte is a typical example of a terminally differentiated leukocyte.

The terms "precursor cell", "progenitor cell" and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, the terms "multipotent", "multipotential" or "multipotentiality" are meant to refer to the capability of a stem cell to differentiate into more than one type of cell.

As used herein, the term "allogeneic" is meant to refer to any material derived from a different mammal of the same species.

As used herein, the term "autologous" is meant to refer to any material derived from an individual and re-introduced to the individual.

As used herein, the term "cell preparation" or "cell preparations" are meant to refer to preparations comprising cells but may contain other substances, such as growth factors, extracellular matrix, etc.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE PREFERRED EMBODIMENT

Figure 1:
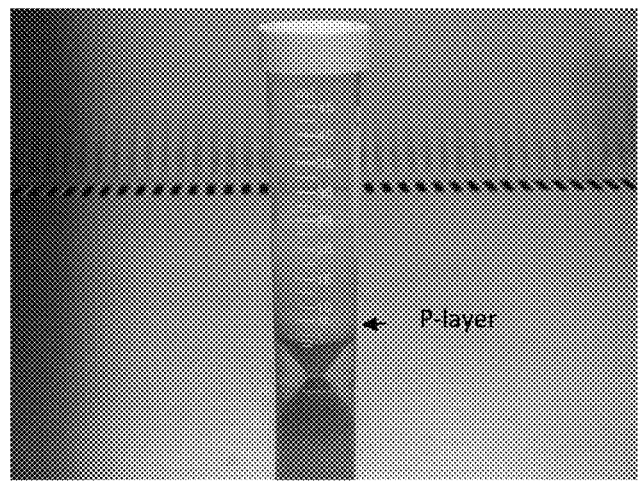
FIG. 1: The P-layer.

In one embodiment, the method of the invention uses an ultrasonic cavitation device having a probe that is placed into contact with the adipose tissue so as to explode or lyse fat cells in the adipose tissue and release the stromal vascular fraction. The particular ultrasonic cavitation device used is not critical to the invention. One suitable selection is the HIELSCHLER ultrasonic processors which is a technologically advanced high intensity ultrasonic processor. This device can safely process a wide range of organic and inorganic materials—from microlitres to litres. Other devices which may be used include Vibra-Cell™ device (Sonics), VASER (SoltaMedical) or QSonica ultrasonic processors.

In another embodiment, adipose tissue in a biologic solution (e.g. phosphate buffered saline solution or normal saline solution) may be placed into a chilled environment (the tissue/cells should not fall below about 2° C.). An ultrasonic cavitation device probe is placed into the adipose tissue and the amplitude is set at about 20%, about 30%, about 40%, about 50%, about 60%, about 70%, about 80%, cycle at about 0.2, about 0.3, about 0.4, about 0.5, about 0.6, about 0.7, about 0.8, about 0.9, for about 10 seconds, about 20 seconds, about 30 seconds, about 40 seconds, about 50 seconds, about 60 seconds, about 1 minute 10 seconds, and about 1 minute 20 seconds, about 1 minute 30 seconds, about 1 minute 40 seconds, about 1 minute 50 seconds, about 2 minutes, about 3 minutes, about 4 minutes, about 5 minutes, about 6 minutes, about 7 minutes, about 8 minutes, about 9 minutes, about 10 minutes. Preferably the amplitude is set at about 50%, cycle about 0.4-0.5. The probe may be adjusted in at different positions in the tube during the operation. The procedure may be conducted in a chilled environment or at room temperature with the amplitude, cycle and time are adjusted to prevent the temperature of the adipose tissue rising above about 43° C. to about 45° C., preferably not rising above 37° C. The duration of the ultrasonic cavitation may operate for a sequenced period of time dependent on the quantity of the adipose tissue, e.g., the probe is raised and lowered for about 1 minute and then for about 40 seconds at two different locations in the tube for larger amounts of adipose tissue, or the probe is raised and lowered for about 1 minute and then for about 30 seconds at the top of the tube or the probe is inserted into the adipose tissue for about 30 seconds, stopped for about 10 seconds, then repeated, then raised the top of the adipose tissue for about 30 seconds for smaller amounts of adipose tissue. The sequence and timing of ultrasonic cavitation (specifically, the amplitude, cycles and time of application) may vary but is determined to the extent of ensuring the optimal cell numbers and viability of the stem cells in the stromal vascular fraction by preventing the adipose tissue temperature from rising above ideally 37° C. or no more than about 43° C. to about 45° C. These parameters can be easily determined by simple trial and error. Typically, the amplitude is about 50%, the cycle is about 0.4 to about 0.5 and the time is about one minute and 30 seconds. If amplitude is increased, the cycle or time can be consequently decreased (or vice versa) to ensure that the temperature of the adipose tissue does not rise above about 43° C. to about 45°. As noted this treatment does not include the addition of collagenase or equivalent enzyme intended to break down collagen as cell dissociation is instead accomplished by ultrasonic cavitation. After ultrasonication there is a thick solution in the tube (which cannot be filtered or easily separated into the stromal vascular fraction) and may be centrifuged.

Centrifugation results in 3 layers—the top lipid layer, the middle floating layer (called the P-layer) containing extra-cellular matrix, adipose cells and stromal vascular cells, and a bottom layer of fluid. The top lipid layer is removed (removal of the lipid layer permits a separation of cells when isotonic fluid is added) and discarded and the remaining contents of the tube mixed well and a solution, typically 0.9% saline, PBS or any other isotonic solution, is added to the tube. Further centrifugation brings about the cells and extra-cellular matrix to fall out and pellet at the bottom, the remaining adipose cells rise to the top of the tube. The pellet contains extracellular matrix and stromal vascular fraction comprising viable and functional stromal/stem cells (including mesenchymal stem cells). The pellet may be filtered through a filter to remove any large debris. The cell solution can be used as is, or further concentrated by a further centrifugation and removal of excess fluid. A sample may be removed for cell counting.

Cell viability and functionality may be determined by cell culture techniques as those familiar with the art. Cells may be counted using a FACs instrument and a fluorescent nucleic binding dye i.e., Guava PCA system and Guavea Viacount.

Typically cell numbers derived from 20 g of adipose tissue using this method are between about 40-200 million cells, i.e., about 2-10 million cells/gram, which is greater than that from collagenase separation which typically results in about 0.5 million cells/gram of adipose tissue.

In another embodiment, the method comprises the following steps:

(a) an ultrasonic cavitation device probe is placed into about 40 g adipose tissue and the amplitude is set at about 50% and the cycle set about 0.4-0.5;

(b) the probe is raised and lowered through the adipose tissue for about 1 minute and then for about 40 seconds at two different locations in the adipose tissue;

(c) the adipose tissue is centrifuged at 800 g/5 min;

(d) the top lipid layer is discarded and the adipose tissue is mixed;

(e) an isotonic solution is added and the adipose tissue is centrifuged at 800 g/5 min;

(f) the resultant cell pellet comprises extracellular matrix and a stromal vascular fraction comprising viable stem cells.

In another embodiment, the method comprises the following steps:

(a) an ultrasonic cavitation device probe is placed into about 40 g adipose tissue and the amplitude is set at about 50% and the cycle set at about 0.4-0.5;

(b) the probe is raised and lowered through the adipose tissue for about 1 minute and then for about 30 seconds at the top of the adipose tissue;

(c) the adipose tissue is centrifuged at 800 g/5 min;

(d) the top lipid is discarded and the adipose tissue is mixed;

(e) an isotonic solution is added and the adipose tissue is centrifuged at 800 g/5 min;

(f) the resultant cell pellet comprises extracellular matrix and a stromal vascular fraction comprising viable stem cells.

In another embodiment, the stem cells are autologous or allogeneic.

The stromal vascular fraction or stromal/stem cells may be directly infused in subjects in need thereof by traditional administration routes, such as intravenous injection or intra-articular injection, or it can be further processed to purify (and expand in culture if desired) desired cell types such as mesenchymal stem cells, or STRO-1+ cells prior to administration.

In some embodiments, stem cells can be isolated, purified or enriched from the stromal vascular fraction by fractionation using unique cell surface antigens and fluorescence activated call sorting (FACS) for expansion in vitro.

In some embodiments the stromal vascular fraction or stromal/stem cells may be cultured with or without differentiation using standard cell culture techniques. The cells may be cultured to a suitable point and viability and yield assessed by standard methods.

In other embodiments, the stromal vascular fraction or stromal/stem cell may be stored for later implantation/infusion (e.g., by cryopreservation). Moderation to long-term storage in a cell bank is also within the scope of this invention.

At the end of processing, the stromal vascular fraction or stromal/stem cells may be loaded into a delivery device, such as a syringe or IV bag, for administration to the recipient by either subcutaneous, intravenous, intramuscular, or intraperitoneal techniques. In other words, cells may be placed into the patient by any means known to persons of ordinary skill in the art, for example, they may be injected into blood vessels for systemic or local delivery, into tissue (e.g., cardiac muscle, or skeletal muscle), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a preformed matrix or adipose tissue-derived or stromal-derived extra-cellular matrix.

The stromal vascular fraction or stromal/stem cells may be applied alone or in combination with other cells, tissue, tissue fragments, demineralized bone, growth factors such as insulin or drugs such as members of the thiaglitazone family, biologically active or inert compounds, resorbable plastic scaffolds, adipose tissue-derived or stromal-derived lattice and/or extra cellular matrix or other additive intended to enhance the delivery, efficacy, tolerability, or function of the population. In certain embodiments of the invention, the cells are administered to a patient with one or more cellular differentiation agents, such as cytokines and growth factors. In other embodiments, the cells are treated with platelet-rich plasma.

In another embodiment, the stromal vascular fraction or stromal/stem cells are administered to a subject to treat or prevent a disease or disorder in the subject.

In another embodiment, the disease or disorder is osteoarthritis, a joint-related inflammatory disorder, an inflammatory arthritis disorder, soft-tissue damage or tears, a cartilage disorder, a bone disorder, an auto-immune disorder, muscle dystrophy, chronic fatigue, a lung disorder, a lung inflammatory disorder, a nervous system disorder, a spinal disorder or a neurological disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1—Preparation of the Adipose Tissue by Liposuction

An excess amount of Tumescent solution (containing, in one litre of normal saline, 1 mg adrenalin, 400 mg to 800 mg lignocaine and 10 mLs of a 8.4% sodium bicarbonate solution), which exceeds the amount of liposuction to be aspirated prior to the liposuction operation, was infused into hypodermic fat layer (tumescent method), and thereafter cannulae having, for example, 2-3 mm of inner diameter (made of metal with aspirator) was used for the liposuction operation. Liposuction operations are well known in the art, and for example, can be referred to in Biyo Seikei Shujutsu Practice 2 (Cosmetic Operation Practice 2), ed. Masanari ICHIDA, Ryusaburo TANINO, and Yoshiaki HOSAKA, published by BUNKODO, pp. 429-469, which is incorporated herein by reference in its entirety.

Aspirated fat was washed with saline. About 50 ml to ten litres of washed aspirate may be generated, and the resultant adipose tissue derived cellular materials used for derivation of stromal vascular fractions.

Example 2—Preparation of Adipose Tissue by Surgery

Fat tissue is obtained by surgery from human subjects who had given their informed consent. Separation was conducted with techniques well known in the art. Briefly, human fat tissue was aseptically separated from fat tissue suctioned from human subjects who had given their informed consent. The resultant adipose tissue derived cellular materials are used for derivation of stromal vascular fractions.

Example 3—Preparation of a Stromal Vascular Fraction Comprising Viable Stem Cells by Ultrasonic Cavitation (Ultrasonic Cavitation at Amplitude 40% and Cycle 0.5 for 2 Minute and 40 Seconds)

1) Adipose tissue derived from liposuction aspirates and 45 ml placed into a 50 ml tube.

2) Excess fluid is removed by centrifuged at 200 g/2 minutes to separate out the excess fluid and adipose tissue. The excess fluid at the base of the tube is removed, typically leaving 40 ml of adipose tissue.

3) (Optional) The tube is placed into a chilled environment and care taken to ensure that the temperature of the tissue/cells does not fall below 2° C.

4) The ultrasonic cavitation device probe Hielschler UP200S is placed into the adipose tissue and the amplitude is set at 50%, cycle 0.5. The probe is raised and lowered for 1 minute and then for 40 seconds at two different locations in the tube (i.e., bottom and top of the tube), rested for 3 minutes and optionally the process repeated. Care is taken to prevent the adipose tissue temperature from rising above 43° C. preferably not above 37° C.

5) After ultrasonication a thick solution is observed in the tube and is centrifuged at 300 g/5 min.

6) After centrifugation there are 3 layers—the top lipid layer, the middle floating layer containing extracellular matrix and stromal vascular cells, and a bottom layer of fluid.

7) The top lipid layer is removed and discarded using a mixing cannula and syringe (removal of the lipid layer permits a separation of cells when isotonic fluid is added) and the remaining contents of the tube mixed well to further disrupt the extra-cellular matrix.

8) An isotonic solution (typically 0.9% saline or PBS) is added to the tube to 50 ml and the tube centrifuged at 600 g/5 mins initiating the cells and extra-cellular matrix to fall out and pellet at the bottom.

9) A large pellet is observed at the bottom of tube containing extracellular matrix and the stromal vascular fraction comprising viable and functional stem cells. The pellet is then removed using a mixing cannula and syringe with approximately 15 ml of fluid, and filtered through a 100 um filter to remove any large debris.

10) The cell solution can be used as is, or further concentrated by a further centrifugation and removal of excess fluid.

Flow cytometry analysis of the isolated stromal vascular fraction shows the presence of viable cells (FIG. 1).

Example 4—Preparation of a Stromal Vascular Fraction Comprising Viable Stem Cells by Ultrasonic Cavitation (Ultrasonic Cavitation at Amplitude 50% and Cycle 0.5 for 1 Minute and 30 Seconds)

1) Adipose tissue derived from liposuction aspirates and 25 ml placed into 2×50 ml centrifuge tubes 2) Excess fluid is removed by centrifuged at 200 g/2 minutes to separate out the excess fluid and adipose tissue. The excess fluid at the base of the tube is removed, typically leaving 20 ml of adipose tissue.

3) (Optional) The tube is placed into a chilled environment or at room temperature and care taken to ensure that the temperature of the tissue/cells does not fall below 2° C.

4) The ultrasonic cavitation device probe Hielschler UP200S is placed into the adipose tissue and the amplitude is set at 50%, cycle 0.5. The probe is raised and lowered for 1 minute and then for 30 seconds at the top for each tube. Care is taken to prevent the adipose tissue temperature from rising above 43° C., preferably not above 37° C.

5) After ultrasonication a thick solution is observed in the tube and is centrifuged at 300 g/5 min.

6) After centrifugation there are 3 layers—the top lipid layer, the middle floating layer containing extracellular matrix and stromal vascular cells, and a bottom layer of fluid.

7) The top lipid layer is removed and discarded using a mixing cannula and syringe, (removal of the lipid layer permits a separation of cells when isotonic fluid is added) and the remaining contents of the tube mixed well to further disrupt the extra-cellular matrix.

8) An isotonic solution (typically 0.9% saline or PBS) is added to the tube to 50 ml and the tube centrifuged at 600 g/5 mins initiating the cells and extra-cellular matrix to fall out and pellet at the bottom.

9) A large pellet is observed at the bottom of tube containing extracellular matrix and the stromal vascular fraction comprising viable and functional stem cells. The pellet is then removed using a mixing cannula and syringe with approximately 15 ml of fluid, and filtered through a 100 um filter to remove any large debris.

10) The cell solution can be used as is, or further concentrated by further centrifugation and removal of excess fluid.

Example 5—Preparation of a Stromal Vascular Fraction Comprising Viable Stem Cells by Ultrasonic Cavitation (Ultrasonic Cavitation at Amplitude 50% and Cycle 0.4 for 1 Minute and 40 Seconds)

1) Adipose tissue derived from liposuction aspirates and 45 ml placed into a 50 ml tube.

2) Excess fluid is removed by centrifuged at 200 g/2 minutes to separate out the excess fluid and adipose tissue. The excess fluid at the base of the tube is removed, typically leaving 40 ml of adipose tissue.

3) The ultrasonic cavitation device probe Hielschler UP200S is placed into the adipose tissue and the amplitude is set at 50%, cycle 0.4. The probe is raised and lowered for 1 minute and then for 40 seconds at two different locations in the tube (i.e., middle and top of the tube), care is taken to prevent the adipose tissue temperature from rising above 43° C., preferably not above 37° C.

4) After ultrasonication a thick solution is observed in the tube and is centrifuged at 800 g/5 min.

5) After centrifugation there are 3 layers—the top lipid layer, the middle floating layer containing extracellular matrix and stromal vascular cells, and a bottom layer of fluid.

6) The top lipid layer is removed and discarded using a mixing cannula and syringe (removal of the lipid layer permits a separation of cells when isotonic fluid is added) and the remaining contents of the tube mixed well to further disrupt the extra-cellular matrix.

7) An isotonic solution (typically 0.9% saline or PBS) is added to the tube to 50 ml and the tube centrifuged at 800 g/5 mins initiating the cells and extra-cellular matrix to fall out and pellet at the bottom.

8) A large pellet is observed at the bottom of tube containing extracellular matrix and the stromal vascular fraction comprising viable and functional stem cells. The pellet is then removed using a mixing cannula and syringe with approximately 15 ml of fluid, and filtered through a 100 um filter to remove any large debris.

9) The cell solution can be used is, or further concentrated by a further centrifugation and removal of excess fluid.

Example 6—Preparation of a Stromal Vascular Fraction Comprising Viable Stem Cells by Ultrasonic Cavitation (Ultrasonic Cavitation at Amplitude 50% and Cycle 0.4 for 1 Minute and 30 Seconds)

1) Adipose tissue derived from liposuction aspirates and 25 ml placed into 2×50 ml centrifuge tubes 2) Excess fluid is removed by centrifuged at 200 g/2 minutes to separate out the excess fluid and adipose tissue. The excess fluid at the base of the tube is removed, typically leaving 20 ml of adipose tissue.

3) The ultrasonic cavitation device probe Hielschler UP200S is placed into the adipose tissue and the amplitude is set at 50%, cycle 0.4. The probe is raised and lowered for 1 minute and then for 30 seconds at the top for each tube. Care is taken to prevent the adipose tissue temperature from rising above 43° C., preferably not above 37° C.

4) After ultrasonication a thick solution is observed in the tube and centrifuged at 800 g/5 min.

5) After centrifugation there are 3 layers—the top lipid layer, the middle floating layer containing extracellular matrix and stromal vascular cells, and a bottom layer of fluid.

6) The top lipid layer is removed and discarded using a mixing cannula and syringe (removal of the lipid layer permits a separation of cells when isotonic fluid is added) and the remaining contents of the tube mixed well to further disrupt the extra-cellular matrix.

7) An isotonic solution (typically 0.9% saline or PBS) is added to the tube to 50 ml and the tube centrifuged at 800 g/5 mins initiating the cells and extra-cellular matrix to fall out and pellet at the bottom.

8) A large pellet is observed at the bottom of tube containing extracellular matrix and the stromal vascular fraction comprising viable and functional stem cells. The pellet is then removed using a mixing cannula and syringe with approximately 15 ml of fluid, and filtered through a 100 um filter to remove any large debris.

9) The cell solution can be used as is, or further concentrated by a further centrifugation and removal of excess fluid.

Example 7—Preparation of P-layer by Ultrasonic Cavitation

1) Adipose tissue derived from liposuction aspirates and 25 ml placed into 2×50 ml centrifuge tubes.

2) Excess fluid is removed by centrifuged at 200 g/2 minutes to separate out the excess fluid and adipose tissue. The excess fluid at the base of the tube is removed, typically leaving 20 ml of adipose tissue.

3) The ultrasonic cavitation device probe Hielschler UP200S is placed into the adipose tissue and the amplitude is set at 50%, cycle 0.4. The probe is raised and lowered for 1 minute and then for 30 seconds at the top for each tube. Care is taken to prevent the adipose tissue temperature from rising above 43° C., preferably not above 37° C.

4) After ultrasonication a thick solution is observed in the tube and is centrifuged at 800 g/5 min.

5) After centrifugation there are 3 layers—the top lipid layer, the middle floating layer containing extracellular matrix and stromal vascular cells (the P layer), and a bottom layer of fluid (FIG. 1).

9) The top lipid layer and bottom fluid layer is removed and the middle P-layer is collected using a mixing cannula.

The P-layer solution can be used as is, or further concentrated by a further centrifugation and removal of excess fluid or diluted with an isotonic solution.

Example 8—Preparation of Expanded Stem Cells

Cells obtained by the method of Example 3 or Example 4 were cultured without differentiation using standard cell culture medium (e.g., alphaMEM typically supplemented with foetal calf serum, human serum or serum free medium). Primary cultures are plated at $1\times10^6$/100 mm and the cells were expanded for 1-2 passages in 5% $CO_2$ or hypoxic environment.

Figure 2:
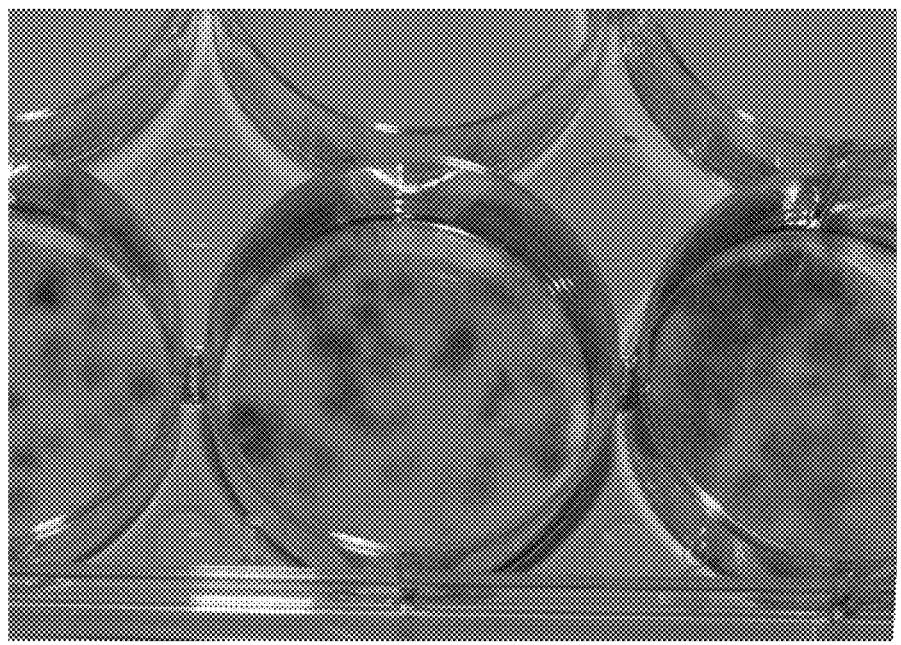
FIG. 2: Giemsa stained colonies of plastic adherent cells from the stromal vascular fraction grown from ultrasonic cavitation treated adipose tissue.
Figure 3:
FIG. 3: Cell culture of mesenchymal stem cells grown from ultrasonic cavitation treated adipose tissue.

Cultures of the isolated stromal vascular fraction from Example 3 shows that viable cells may be grown and expanded (FIG. 2) which have the morphology of mesenchymal stem cells (FIG. 3).

Figure 4:
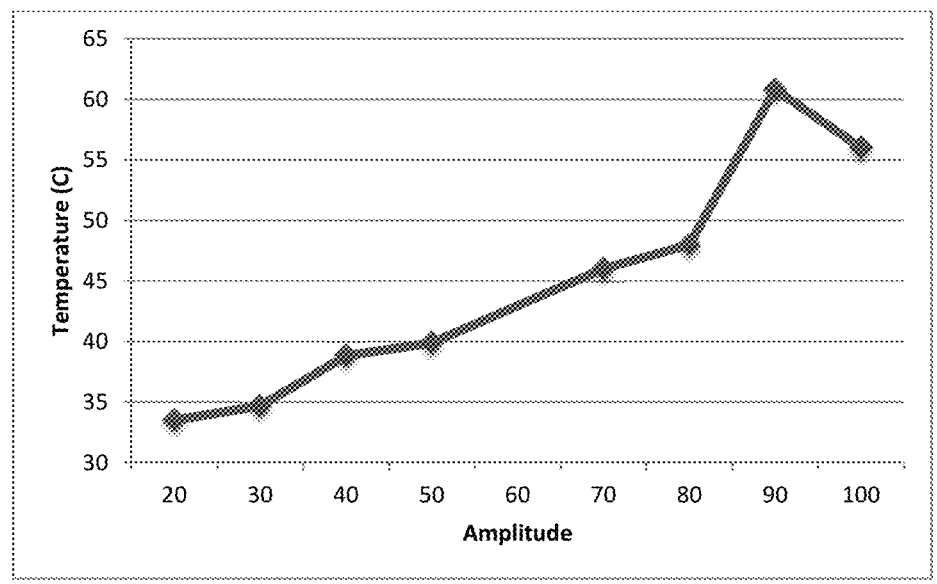
FIG. 4: Effect of ultrasonic cavitation amplitude settings on temperature of adipose tissue—20 grams of adipose tissue treated for 1.sup.½ minutes with cycle setting 0.4.
Figure 5:
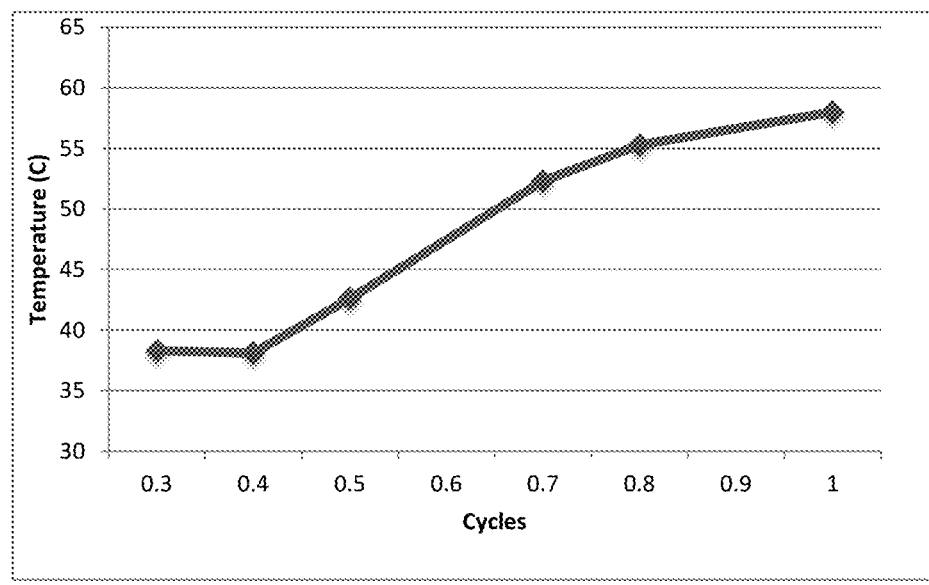
FIG. 5: Effect of ultrasonic cavitation cycle settings on temperature of adipose tissue—20 grams of adipose tissue treated for 1.sup.½ minutes with amplitude setting 50%.

Example 9—Effect of Ultrasonic Cavitation Amplitude and Cycle on Adipose Tissue Temperature and Cell Viability Experiments were performed to assess the effect of ultrasonic cavitation amplitude and cycle on adipose tissue temperature (FIGS. 4 and 5). The results demonstrated that the temperature of the adipose tissue rose above 43° C. at:
amplitudes above 50% (at cycles 0.4 and time 1 minute 30 seconds)—see FIG. 4; and
cycles above 0.5 (at amplitude 50% and time 1 minute 30 seconds)—see FIG. 5.

Figure 6:
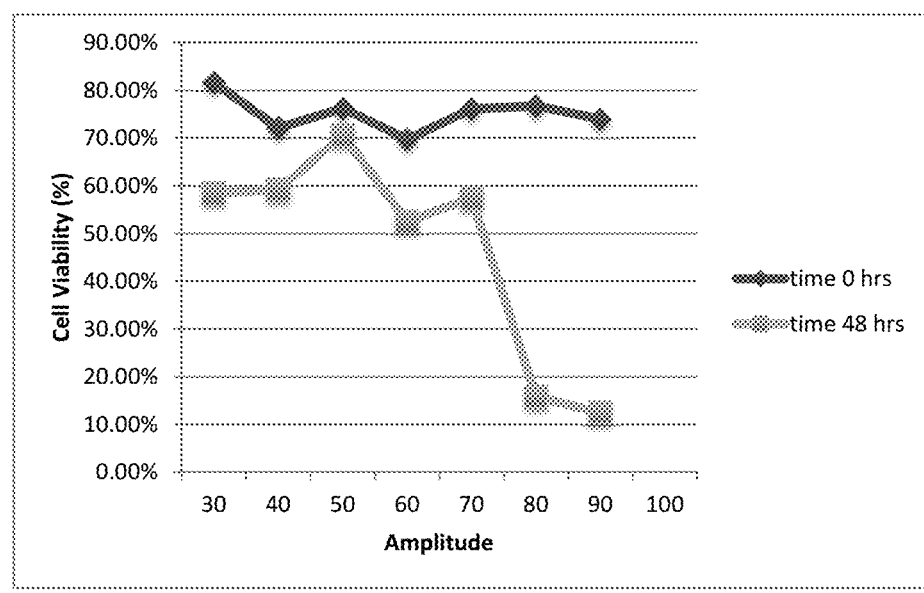
FIG. 6: Effect of ultrasonic cavitation amplitude on stromal vascular fraction cell viability—20 grams of adipose tissue treated for 1.sup.½ minutes with cycle setting 0.4.
Figure 7:
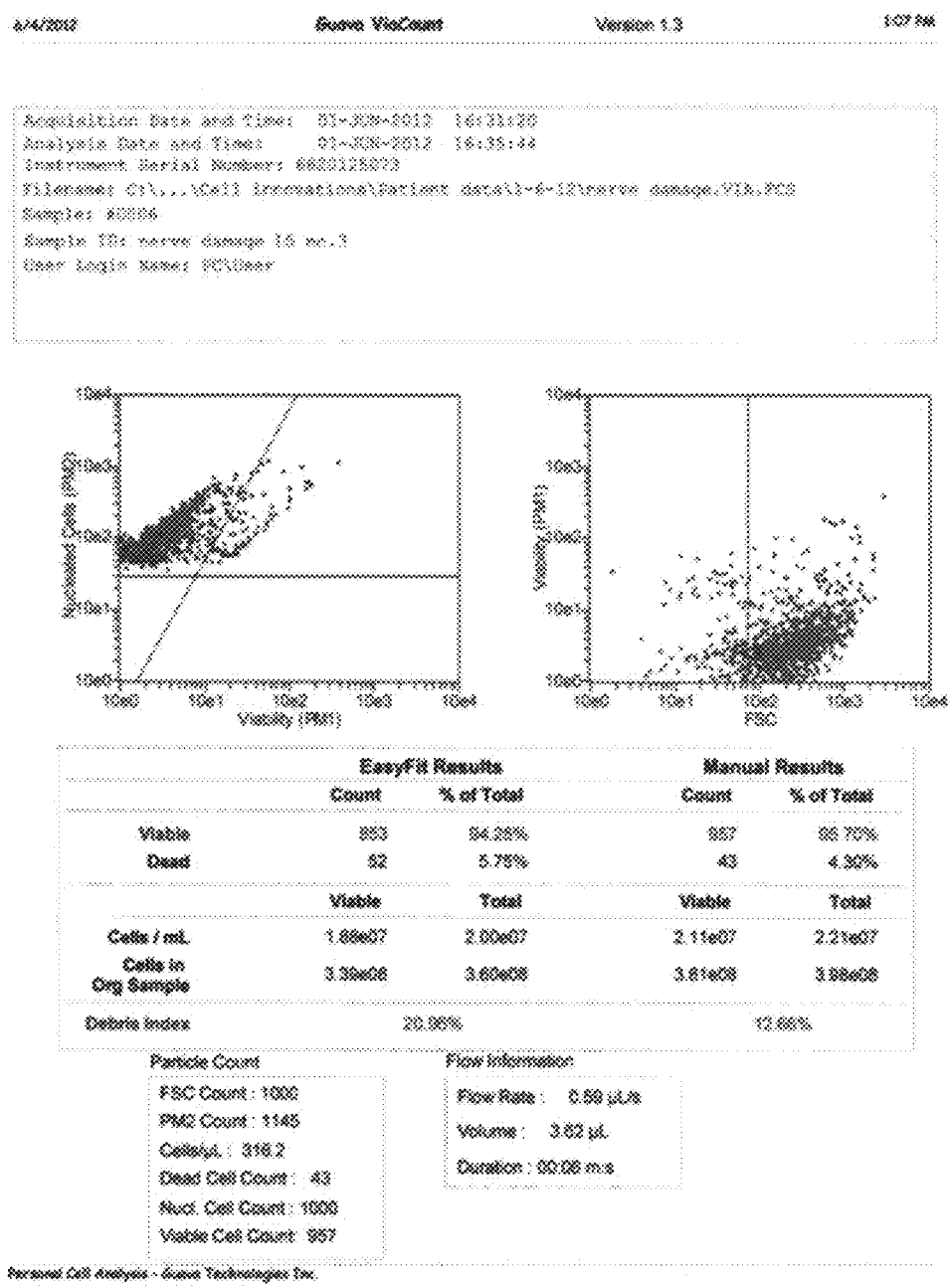
FIG. 7: Flow cytometry analysis of cells obtained from ultrasonic cavitation treated adipose tissue—cell count by fluorescent nuclei of 40 grams of adipose tissue separated by ultrasonic cavitation.

Experiments were also performed to assess the effect of ultrasonic cavitation amplitude on cell viability immediately following cavitation and after 48 hours of culture. While increased amplitude did not have a noticeable effect on cell viability immediately following cavitation (FIGS. 6 and 7), the viability of cultured cells at 48 hours decreased significantly with amplitudes over 50% (FIG. 6).

Example 10—Preparation of Platelet-Rich Plasma and Plasma Rich Growth Factors

1) Blood is collected prior to anaesthetic. 2×9 mL acid citrate dextrose (ACD-A) blood collection tubes (BD vacutainer) are filled with blood (by vacuum pressure). The blood is drawn using an 18 G needle or larger to avoid activating the platelets by shearing. The contents of the blood tubes are mixed by inverting the tubes 3-4 times.

2) The ACD-A blood filled tubes are centrifuged at 450 g×10 min.

3) The plasma layer (the top layer) is removed from each tube with the same transfer pipette and placed into 15 mL sterile tube. The blood should not be disturbed and the thin layer of white cells resting on the should be avoided. It is best to leave a 5 mm layer of plasma above the red blood cells. This plasma containing enriched platelets (PRP) can be used as is or further treated as below.

4) The tube containing the plasma is centrifuged for 2000 g/10 min—a small pellet of platelets at the bottom of the tube should form.

5) The top platelet poor plasma should be removed with a transfer pipette down to 1.5 mL and discarded. The pellet should be resuspended in the remaining 1.5 mL using the same transfer pipette. This is the platelet-rich plasma (PRP).

6) PRP may be used as is or if desired clotted with 150 μl of the calcium gluconate (1 mL syringe and needle) added to the PRP and mixed well. The tube should be placed in the warm water bath (37° C.—without shaking) or left at room temperature for longer period of time. The PRP should form a solid gel.

7) After solidification, the PRP can be left at either 37° C. (to speed up the process) or room temperature to partially dissolve over the next 1-2 hr for when you are ready to add it the cells—this is now known as plasma rich growth factors (PRGF).

Example 11—Preparation of Stromal Vascular Fraction or P-layer for Injection

The cells obtained by the methods of examples 3 to 9 may be treated with PRP or PRGF prior to injection. The PRGF typically 2.5 ml is added directly to the cell pellet prior to injection. The cells and PRGF are applied as example 12. If PRP is to be used with the stromal/stem cells (typically 5 mls) it may be added with the cells just prior to injection as it may start to initiate a solid gel or it may be injected separately just after stromal vascular fraction administration.

Example 12—Administration of the Stromal Vascular Fraction of Adipose Tissue to Patients with Osteoarthritis The Western Ontario and McMaster Universities Arthritis Index (WOMAC) is a widely used, proprietary set of standardized questionnaires used by health professionals to evaluate the condition of patients with osteoarthritis of the knee and hip, including pain, stiffness, and physical functioning of the joints.

The WOMAC is among the most widely used assessments in arthritis research. The WOMAC measures five items for pain (score range 0-20), two for stiffness (score range 0-8), and 17 for functional limitation (score range 0-68). An arthritic pain scoring system ranging from 0-no pain/disability to 96—most severe pain/disability The WOMAC consists of 24 items divided into 3 subscales:
- Pain (5 items): during walking, using stairs, in bed, sitting or lying, and standing
- Stiffness (2 items): after first waking and later in the day
- Physical Function (17 items): stair use, rising from sitting, standing, bending, walking, getting in/out of a car, shopping, putting on/taking off socks, rising from bed, lying in bed, getting in/out of bath, sitting, getting on/off toilet, heavy household duties, light household duties.

Hip dysfunction and Osteoarthritis Outcome Score (HOOS) contains measurement qualities to evaluate patients with hip osteoarthritis (OA) or total hip replacement (THR). HOOS is intended to be used for hip disability with or without osteoarthritis (OA). HOOS consists of 5 subscales; Pain, other Symptoms, Function in daily living (ADL), Function in sport and recreation (Sport/Rec) and hip related Quality of life (QOL).

Patient 1—Osteoarthritis of the Hips

The stromal vascular fraction of adipose tissue was prepared according to Example 3, treated with PRGF and administered by intra-articular injection into each hip ($84 \times 10^6$ cells) and intravenous injection ($130 \times 10^6$ cells). The patient's pre-treatment HOOS score was 102 pre-treatment and at 5 weeks post-treatment the HOOS score was reduced to 23—an improvement of 77%.

Patient 2—Osteoarthritis of the Knees

The stromal vascular fraction of adipose tissue was prepared according to Example 3, treated with PRGF and administered by intra-articular injection into each knee ($100 \times 10^6$ cells) and intravenous injection ($79 \times 10^6$ cells). The patient's pre-treatment WOMAC score was 59 and at 4 weeks post-treatment the WOMAC score had reduced to 28—an improvement of 61%.

Patient 3—Osteoarthritis of the Knees

The stromal vascular fraction of adipose tissue was prepared according to Example 3 except settings were amplitude 90% and cycle 0.9 for 3 minutes (adipose tissue cooled with 20° C. gel packs to prevent temperature rising above 43° C.), treated with PRGF and administered by intra-articular injection into each knee ($100 \times 10^6$ cells) and intravenous injection ($236 \times 10^6$ cells). The patient's pre-treatment WOMAC score was 37 and at 11 weeks post-treatment the WOMAC score had reduced to 7—an improvement of 81%.

Patient 4—Osteoarthritis of the Knees

The stromal vascular fraction of adipose tissue was prepared according to Example 4, treated with PRP and administered by intra-articular injection into each knee ($86 \times 10^6$ cells) and intravenous injection ($86 \times 10^6$ cells). The patient's pre-treatment WOMAC score was 39 and six weeks post-treatment the WOMAC score had reduced to 17—an improvement of 56%.

Patient 5—Osteoarthritis of the Knees

The stromal vascular fraction of adipose tissue was prepared according to Example 6, and administered by intra-articular injection into each knee ($175 \times 10^6$ cells) and intravenous injection ($150 \times 10^6$ cells). The patient's pre-treatment WOMAC score was 38 and 2 months post-treatment the WOMAC score had reduced to 8—an improvement of 78%.

Patient 6—Osteoarthritis of the Knees

The stromal vascular fraction of adipose tissue was prepared according to Example 5, and administered by intra-articular injection into each knee ($85 \times 10^6$ cells) and intravenous injection ($85 \times 10^6$ cells). The patient's pre-treatment WOMAC score was 56 and 7 months post-treatment the WOMAC core had reduced to 28—an improvement of 50%.

Example 13—Administration of the P-Layer to Patients with Osteoarthritis

Patient 7—Osteoarthritis of the Knees

P-layer cells (5 ml) were prepared according to Example 7 and administered by intra-articular injection the knee and intravenous injection ($170 \times 10^9$ cells). The patient's pre-treatment WOMAC score was 58 and 3 months post-treatment the WOMAC score had reduced to 10—an improvement of 82%

Patient 8—Osteoarthritis of the Knees

P-layer cells (2.5 ml) were prepared according to Example 7 and administered by intra-articular injection the left knee and intravenous injection ($200 \times 10^6$ cells). The patient's pre-treatment WOMAC score was 37 and 2 months post-treatment the WOMAC score had reduced to 2—an improvement of 94%

Example 14—Administration of the Stromal Vascular Fraction of Adipose Tissue to Patients with Other Diseases Patient 9—Rheumatoid Arthritis The stromal vascular fraction of adipose tissue was prepared according to Example 5 (with the following alterations—amplitude 90%, cycle 0.2, 4 minutes) and administered by intravenous injection ($276 \times 10^7$ cells). First week patient felt well but then rheumatoid arthritis reflared. Patient felt more alert.

| Method | ID | Condition | Cell number and delivery | Results |
|---|---|---|---|---|
| Example 5 | 10 | Motor Neurone Disease | IV $130 \times 10^6$ with repeat injections of cryopreserved cells | weight stable 11 months from treatment and walking improved. Feels well in himself |
| Example 5 | 11 | Acute Tear Anterior Cruciate Ligament (ACL) | IA $169 \times 10^6$ Second IA injection 6 months later $91 \times 10^6$ | Re-attachment and complete heal of the torn ligament back to cycling running etc marathons |

| Method | ID | Condition | Cell number and delivery | Results |
|---|---|---|---|---|
| Example 5 | 12 | Rotator Cuff And Dystonia | IA 23 × 10$^6$ each shoulder & 100 × 10$^6$ IV. 2nd IV 5 months later 250 × 10$^6$ cells | Next night slept well as no shoulder pain and with the right hand open. Dystonia improved after 2nd injection at 3 months |
| Example 5 | 13 | Multiple Sclerosis | IV 389 × 10$^6$ & IA 150 × 10$^6$ | Improvement in bladder function and sleeping better, more energy and stamina |
| Example 5 | 14 | Facioscapulohumeral Dystrophy (FSHD) | IV 180 × 10$^6$ | multiple treatments performed a week apart, no improvements seen |
| Example 5 | 15 | Spastic Parapleger | IV 80 × 10$^6$ | arm/hand strength have both imprvoed at 1-2 month stage |
| Example 6 | 16 | Rheumatoid Artritis | IV 10 × 10$^6$ | Pain eased off, RF dropped, off all medications. Lasted for a month. Temporary improvement |
| Example 6 | 17 | Multiple Sclerosis | IV 200 × 10$^6$ | Two weeks later was stronger physically and had improved bladder/bowel function. 6 months later maintaining progress |
| Example 6 | 18 | Muscular Dystrophy | IV 100 × 10$^6$ then weekly 7 × 113 × 10$^6$ | 2 months later improved strength, walking better (balance) and has more muscle tone. |
| Example 6 | 19 | Scleraderma | IV 111 × 10$^6$ then monthly IV treatments 55 × 10$^6$ | Felt stronger 2 days post op, Lethargy was shown to also improve |
| Example 5 | 20 | Chronic Fatigue | IV 1.9 × 10$^6$ | More energy noted 2 days post op, one month later energy levels have fluctuated |
| Example 6 | 21 | Anklylosing Spondylitis, Chronic Fatigue Syndrome | 1 × 10$^6$ IV and .5 × 10$^6$ IA each shoulder | Shoulders improved, fatigue no improvement |
| Example 6 | 22 | Cerebrospinal Ataxia | IV 200 × 10$^6$ followed 5.3 × 10$^6$ IA by 100 × 10$^6$ at 3 and 4 months | Double vision did not change in first 3 months. After 2nd and 3rd an improvement seen in a number of symptoms |
| Example 6 | 23 | Nerve Damage | IV 463 × 10$^6$ | 2 months later movement has improved and has regained some sensation |
| Example 6 | 24 | Bilateral Foot Drop | IV 100 × 10$^6$ IA 50 × 10$^6$ each knee. 2nd injection IA 74 × 10$^6$ 2 months later | Some movement in the legs next day. After second injection tingling in legs |
| Example 6 | 25 | Asthma | IV 200 × 10$^6$ & IA 200 × 10$^6$ | Sputum coming up easier, 1 month later, continued joint improvements and breathing easier. |

The invention claimed is:

1. A method of isolating a stromal vascular fraction comprising viable stromal/stem cells from adipose tissue, the method comprising treating the adipose tissue with ultrasonic cavitation about 90 seconds to about 8 minutes with an amplitude and cycle corresponding to that of a Hielscher UP200S ultrasonic device set at an amplitude of about 20% to about 70%, and a cycle of about 0.2 to about 0.8 seconds; wherein in said method, the amplitude does not exceed 70%, the cycle does not exceed 0.8 seconds, the duration of cavitation does not exceed 8 minutes, and the temperature of the adipose tissue does not exceed about 43° C. to about 45° C.

2. The method according to claim 1 wherein the temperature of the adipose tissue during ultrasonic cavitation is maintained at a temperature that ensures the viability of the stromal/stem cells.

3. The method according to claim 1 wherein the adipose tissue is treated with ultrasonic cavitation for about 1 minute and 30 seconds to about 1 minute and 40 seconds with an ultrasonic device set at an amplitude of about 50% and a cycle of about 0.4 to about 0.5 seconds.

4. The method according to claim 1 wherein the lipid layer resulting from the ultrasonic cavitation is removed before addition of an isotonic solution.

5. The method according to claim 1, comprising the following steps:
 (a) placing an ultrasonic device probe into adipose tissue, wherein the ultrasonic device is set at an amplitude of about 50% and a cycle of about 0.4 to about 0.5 seconds;
 (b) raising and lowering the probe through the adipose tissue for about 1 minute and then for about 40 seconds at two different locations in the adipose tissue;
 (c) centrifuging the adipose tissue at 800 g for 5 min;
 (d) discarding the top lipid layer and mixing the adipose tissue; and
 (e) adding an isotonic solution and centrifuging the adipose tissue at 800 g for 5 min, wherein the resultant cell pellet comprises extracellular matrix and a stromal vascular fraction comprising viable stem cells.

6. The method according to claim 1, comprising the following steps:
(a) placing an ultrasonic cavitation device probe into adipose tissue, wherein the ultrasonic device is set at an amplitude of about 50% and a cycle of about 0.4 to about 0.5 seconds;
(b) raising and lowering the probe through the adipose tissue for about 1 minute and then for about 30 seconds at the top of the adipose tissue;
(c) centrifuging the adipose tissue at 800 g for 5 min;
(d) discarding the top lipid layer and mixing the adipose tissue; and
(e) adding an isotonic solution and centrifuging the adipose tissue at 800 g for 5 min,
wherein the resultant cell pellet comprises extracellular matrix and a stromal vascular fraction comprising viable stem cells.

7. The method according to claim 1, wherein the isolated stromal vascular fraction is cultured.

8. The method according to claim 7, wherein the cultured stromal vascular fraction is grown and expanded.

9. The method according to claim 8, wherein the cultured stromal vascular fraction comprises mesenchymal stem cells.

* * * * *